US007208180B2

(12) United States Patent
Kiliaan et al.

(10) Patent No.: US 7,208,180 B2
(45) Date of Patent: Apr. 24, 2007

(54) METHOD AND PREPARATION FOR THE PREVENTING AND/OR TREATING VASCULAR DISORDERS AND SECONDARY DISORDERS ASSOCIATED THEREWITH

(75) Inventors: Amanda Johanne Kiliaan, Wageningen (NL); Robert Johan Joseph Hageman, Waddinxveen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/899,922

(22) Filed: Jul. 9, 2001

(65) Prior Publication Data

US 2002/0040058 A1 Apr. 4, 2002

Related U.S. Application Data

(63) Continuation-in-part of application No. 09/566,386, filed on May 8, 2000, now abandoned.

(51) Int. Cl.
 *A61K 36/00* (2006.01)
 *A61K 36/38* (2006.01)
 *A61K 36/16* (2006.01)
 *A61K 36/752* (2006.01)

(52) U.S. Cl. .................. 424/725; 424/730; 424/752; 424/736; 514/165; 514/185; 514/494; 514/557; 514/822

(58) Field of Classification Search ............... 424/725, 424/730, 752, 736; 514/165, 557, 822, 494, 514/261, 556, 561, 185
See application file for complete search history.

(56) References Cited

U.S. PATENT DOCUMENTS

| 4,897,380 | A | * | 1/1990 | Pollack et al. |
| 5,401,730 | A | * | 3/1995 | Sauvage et al. |
| 5,753,703 | A | * | 5/1998 | Cavazza et al. |
| 5,820,867 | A | * | 10/1998 | Bewicke |
| 5,922,704 | A | * | 7/1999 | Bland |
| 5,965,413 | A | * | 10/1999 | Sakai et al. |
| 6,042,849 | A |   | 3/2000 | Richardson et al. |
| 6,096,317 | A | * | 8/2000 | Desantis et al. |
| 6,200,607 | B1 | * | 3/2001 | Bridgeman |
| 6,344,482 | B1 | * | 2/2002 | Stoll et al. |
| 6,369,042 | B1 | * | 4/2002 | Oberthur et al. |

FOREIGN PATENT DOCUMENTS

| DE | 28 24 362 | 12/1979 |
| EP | 0 652 012 | 5/1995 |
| EP | 0 721 742 | 7/1996 |
| EP | 0 843 972 | 5/1998 |
| FR | 2 773 484 | 7/1999 |
| GB | 2 327 347 | 1/1999 |
| JP | 63208524 A | * 8/1988 |
| WO | WO 89/02737 | 4/1989 |
| WO | WO 93/19624 | 10/1993 |
| WO | WO 94/27628 | 12/1994 |
| WO | WO 97/39749 | 10/1997 |
| WO | WO 97/39759 | * 10/1997 |
| WO | WO 98/48788 | * 11/1998 |
| WO | WO 99/37155 | 7/1999 |
| WO | WO 99/66914 | * 12/1999 |
| WO | WO 01/84961 | 11/2001 |

OTHER PUBLICATIONS 1998-140919, Jan. 1998, Derwent, Sagami Chem Res Centre.*
1996-252856, May 1996, Derwent, Horrobin.*
1995-224142, Jun. 1995, Derwent, Hashim.*
1997-516044, Apr. 1998, Derwent, Bozoky et al.*
1995-145875, Aug. 1993, Derwent, Ponomareva et al.*
1989-114242, Apr. 1989, Derwent, Cade et al.*
1995-400907, Oct. 1995, Derwent, Ogawa.*
1998-406051, Jun. 1998, Derwent, Yanai.*
2000-148134, Nov. 1999, Derwent, He.*
Derwent 1995-015698, Dec. 1994, Derwent, Naito et al.*
Derwent 1992-408041, Dec. 1992, Derwent, Bormann et al.*
Derwent 1997-017294, Oct. 1996, Derwent, Takeda Chem Ind Ltd.*
Maggioni et al., "Effects of phosphatidylserine therapy in geriatric patients with depressive disorders", Acta Psychiatr Scand, Mar. 1990, 81 (3):265-70, abstract.*
Fugh-Berman, et al., "Dietary supplements and natrula products as psychotherapeutic agents", Psychosom Med, Sep. 1999, 61(5):712-28.*

* cited by examiner

*Primary Examiner*—Ruth A. Davis
(74) *Attorney, Agent, or Firm*—Gilberto M. Villacorta; Sunit Talapatra; Foley & Lardner LLP

(57) ABSTRACT

The present invention relates to a method for the prevention and/or treatment of vascular disorders and/or secondary disorders associated therewith, such as depression. The method according to the invention comprises the oral administration of a preparation which contains at least the following fractions:
 a) long chain polyunsaturated fatty acids;
 b) at least two different phospholipids selected from the group consisting of phosphatidylserine, phosphatidylinositol, phosphatidylcholine and phosphatidylethanolamine and
 c) one or more compounds which are a factor in methionine metabolism, which compounds are selected from the group consisting of folate, vitamin B12, vitamin B6, magnesium and zinc or equivalents thereof.

The invention also relates to a preparation for oral dosage comprising:
 at least 120 mg of long chain polyunsaturated fatty acids;
 at least 200 mg phospholipids;
 at least 200 μg folate; and
 at least 0.1 mg hypericin and/or at least 100 mg extract of *Withania somnifera*.

18 Claims, No Drawings

METHOD AND PREPARATION FOR THE PREVENTING AND/OR TREATING VASCULAR DISORDERS AND SECONDARY DISORDERS ASSOCIATED THEREWITH

This application is a contiuation-in-part of Ser. No. 09/566,386 filed May 8, 2000 now abandoned.

BACKGROUND OF THE INVENTION

The present invention relates to a method for the prevention and/or treatment of vascular disorders and secondary disorders associated therewith, such as depression. The invention is also concerned with a preparation that can be used in the prevention and/or treatment of the aforementioned disorders.

The vascular system in the human body is well described in the art. An important part of the system are the blood vessels, that generally are divided in arteries and veins, dependent whether they transport blood to or from the heart. They vary in size from large (e.g. the aorta) to very small (capillaries). From an anatomical point of view larger blood vessels in general comprise as observed from the lumen side:
1. the tunica intima, that consists of a smooth (mono)layer of endothelial cells and a subendothelial layer that consists of a loose layer of connective tissue,
2. the tunica media, which consists of a layer of (innervated) smooth muscle cells and elastic fibers, and
3. the tunica adventitia which is composed of loosely woven collagen fibers, which are infiltrated by tiny lymphatic and blood vessels.

The endothelial cells in the tunica intima are in direct contact with blood and have a barrier function for the underlying tissue. This barrier function includes selective transport of components from blood to the underlying tissue and vice versa, and protection of the underlying tissue. Endothelial cells get easily damaged due to a wide variety of causes like mechanic forces or interaction with stressor components such as classic anaphylatoxins, and components that may occur in the blood, such as homocysteine or components that result from treatment with certain types of drugs (e.g. chemotherapeutics). Vascular permeability can further be increased by a wide variety of humoral- and cell-derived mediators.

Endothelial dysfunction can result in a wide range of disorders. Damage to the endothelial layer can disturb the physiological functions thereof such as transport properties and expose the underlying tissue to stressors. Monocytes may migrate to these damaged spots, get caught by adhesion molecules, differentiate into macrophages, which, when activated, may start up an inflammatory reaction. Due to this reaction cytokines may be released, which may trigger the release of reactive oxygen species, or change coagulation behaviour of blood components. This may result in occurrence of plaques in the arteries, which may ultimately result in hypertension, atherosclerosis and (later) arteriosclerosis.

Atherosclerosis may lead to an impaired blood supply to tissue, which may then become ischaemic. This may lead to damage to cells and even apoptosis of the cells that depend on the oxygen and nutrient supply via these blood vessels. Tissue that has become ischaemic may thus lose functional capacity.

There is increasing evidence that depression, and in particular late-life depression, are caused by or associated with vascular disorders. Cerebral white matter lesions are presently thought to represent vascular abnormalities. White matter lesions have been related to affective disorders and a history of late-onset depression in psychiatric patients. Their relation with mood disturbances in the general population is not clearly understood. For the majority of persons with a depression syndrome the age of onset is in the late twenties, but it is also common to have an onset after age forty. Between 1 and 2% of elderly persons suffer from major depression. A different aetiology is suggested for the depression in late life. It has been suggested that a cerebro-vascular component is probably more important in the aetiology of late-life depression than genetic of psychological factors. Various associations between depression and stroke or hypertension have been found the last 5 years. Lowering hypertension may reduce depression in older depressed people suffering from hypertension/atherosclerosis.

The following articles report on correlations observed between vascular disorders and depression:

Rao R., "Cerebrovascular disease and late life depression: an age old association revisited", Int J Geriatr Psychiatry. (2000) May; 15(5):419–33. Review.

de Groot J C, de Leeuw F E, Oudkerk M, Hofman A, Jolles J, Breteler M M, "Cerebral white matter lesions and depressive symptoms in elderly adults", Arch Gen Psychiatry (2000) November; 57(11):1071–6

Krishnan K R, Doraiswamy P M, Clary C M, "Clinical and treatment response characteristics of late-life depression associated with vascular disease: a pooled analysis of two multicenter trials with sertraline". Prog Neuropsychopharmacol Biol Psychiatry. (2001) February; 25(2):347–61.

Lloyd A J, Grace J B, Jaros E, Perry R H, Fairbairn A F, Swann A G, O'Brien J T, McKeith, Depression in late life, cognitive decline and white matter pathology in two clinico-pathologically investigated cases", Int J Geriatr Psychiatry. (2001) March; 16(3):281–7

Depression and related disorders, sometimes referred to as "mood disorders", can severely impair functioning in normal life of people suffering therefrom, leading to decreased happiness for the persons suffering therefrom but also influencing the people in their surroundings. In the worst cases these disorders can lead to violence or suicide.

Depression and related disorders can be distinguished by short periods of depression or fluctuating heavy moods and longer periods of more severe mood disorders. The latter periods can be caused by psychosis or disturbance of the personality causing extreme behaviour. Examples are bipolar or unipolar depression, schizophrenia and ADHD.

Other causes of depression can be extremely stressful external factors such as loss of a relative, which can disturb the mental balance. Also hormonal changes such as occur during menstruation or menopause can cause longer or shorter periods of emotional distress.

Further it has been noted that certain groups in society, such as elderly, suffer more from depression. This could be related to other causes, beside those mentioned above, including certain changes in the brain of these groups of people. In addition it has been found that depression is frequently encountered in individuals who suffer from neurological disorders, such as dementia and Parkinson's disease.

Beside psychological therapy, which is not effective for every type of patient and chemical drugs, which can be addictive and have severe side effects, no treatment is available.

For the prevention and treatment of vascular disorders no suitable therapy is available either. Vascular disorders and the consequences thereof are a major cause of death in the Western countries. At present vascular disorders are treated by prescribing specific diets that are restricted in cholesterol, saturated fatty acids and in some cases sodium content and by administering drugs that are designed to lower blood pressure (e.g. diuretics), and plasma levels of cholesterol e.g. statins (or oilier compounds that are able to inhibit the activity of HMG-CoA reductase).

Though some of the treatments are indeed effective in treating part of the phenomena associated with vascular problems, the treatments are not 100% effective in solving the real problem (the cause) and they may demonstrate undesired systemic side effects.

PRIOR ART

Vascular endothelial cells and their function in the blood vessel have been studied for a long time. Many details about biochemical processes that occur in these cells have been published as well.

Recently Chang published in vitro data about the effect of pyridoxal-5-phosphate on human umbilical vein endothelial cells that "suggested that vitamin B6 protects endothelial cells by enhancing the beneficial function and preventing cell injury which are responsible for the initiation and the disease process of atherosclerosis". See Chang S. J. Nutrition Research, 1999, 19 (11), 1613–1624; "Vitamin B6 protects vascular endothelial injury by activated platelets".

The structure of cell membranes has been studied; many different components appear to be part of the membrane, such as lipids, proteins and cholesterol. Cholesterol appears to be important for the cell membrane, It decreases the fluidity of the outer cell membrane. It also is able to capture some radicals and is claimed to stop self-propagating radical chain reactions in the cell membrane. It is currently thought that vascular disorders should be treated with cholesterol lowering diets. However, it is not recognised that some forms of cholesterol, in particular plasma cholesterol, could be important in the repair mechanisms associated with vascular damage.

EP 0213724 discloses the use of phosphatidylcholine and phosphatidylethanolamine for membrane fluidisation.

Citric acid and/or citrates are widely used in food manufacture as taste modifier, acidifier and product stabiliser. U.S. Pat. Nos. 5,234,702 and 5,077,069 disclose the use of citric acid as a synergetic component for the antioxidant action of ascorbyl palmitate, beta-carotene and tocopherol.

WO 99/21565 discloses the use of any Kreb's cycle intermediate selected from citric acid, aconitic acid, isocitric acid, α-ketoglutaric acid, succinic acid, fumaric acid, malic acid and oxaloacetate or precursors thereof for treating disorders that are characterised by a decreased level of oxidative metabolism (page 5, line 25), in particular disorders of the nervous system but also of cardiovascular diseases. In particular precursors of oxaloacetate are preferred (page 7, line 10). No reference is made to beneficial effects of administration of these components on vasoendothelial cells, nor to additional effects that could be obtained by including phopholipids or LC-PUFA's in the composition.

In WO 00/00042 of the Applicant it is described that a combination of folic acid, vitamin B6, B12 and optionally tryptophan can be used for improving senses of well-being, control of feeling of pain and improvement of mood, sleeping behaviour, or treatment or prevention of other serotonin or melatonin mediated disorders. In EP 951842 of Applicant a formula for infants containing protein providing tryptophan is described.

SUMMARY OF THE INVENTION

The present inventors have now found a method and a preparation for the treatment of vascular disorders that is effective because it provides activity on the function of the tunica intima and endothelial cells in general, which is important for influencing the aetiology and development of a wide range of vascular disorders and several other secondary disorders, in particular depression.

Thus, the present invention provides a method for the prevention and/or treatment of vascular disorders and/or secondary disorders associated therewith, said method comprising the administration of a preparation which contains at least the following fractions:

a) long chain polyunsaturated fatty acids;
b) phospholipids, which fraction contains at least two different phospholipids selected from the group consisting of phosphatidylserine, phosphatidylinositol, phosphatidylcholine and phosphatidylethanolamine and c) compounds which are a factor in methionine metabolism, which fraction contains at least one member selected from the group consisting of folate, vitamin B12, vitamin B6, magnesium, and zinc or equivalents thereof. Throughout this document the term "folate" also encompasses folic acid.

The above method may advantageously be used to prevent and/or treat vascular disorders and secondary disorders associated therewith in mammals, in particular humans, cattle and pets. Most preferably the present method is used to prevent and/or treat such disorders in humans.

The preparation of the invention can be a pharmaceutical, dietetic as well as a nutritional preparation. The products can have the form of a liquid, powder, bar, cookie, sweetie, concentrate, paste, sauce, gel, emulsion, tablet, capsule, etc. to provide the daily dose of the bioactive components either as a single or in multiple doses. The products can be packaged by applying methods known in the art, to keep the product fresh during shelf life and allow easy use or administration.

DETAILED DESCRIPTION OF THE INVENTION

The combined oral administration of the aforementioned fractions was found to be effective in the treatment and prevention of vascular and related disorders on different levels, in particular on the level of the tunica intima and endothelial cells in general. Fraction a) contains long chain polyunsaturated fatty acids, preferably Ω-3 and/or Ω-6 fatty acids. The fatty acids can be free fatty acids, but are preferably bound to a suitable backbone, for instance in the form of a triglyceride. They can also be in the form of phopholipids as will be described later. The term oral administration also encompasses administration through an oral feeding tube.

The function of fraction a) is to modulate inflammatory processes that may occur in vessel walls and cerebral tissue, to normalise plasma cholesterol levels, especially LDL-cholesterol levels and revert the atherosclerotic process and to increase fluidity of neuronal, erythrocyte and blood vessel membranes. It was found that especially a mixture of Ω-3 and Ω-6 long chain polyunsaturated fatty acids (LCPUFA's) should be included in a ratio of Ω-3 fatty acids to Ω-6 fatty acids of about 2.5 to 5.5 wt/wt.

Preferred Ω-3 LCPUFA's are eicosapentaenoic acid (EPA) and docosahexaenoic acid (DHA). Best results are obtained when DHA and EPA are included in about equimolar amounts, for example a ratio of DHA to EPA of 0.5 to 2 wt/wt. Preferred Ω-6 LCPUFA's are dihomogammalinolenic acid (DHGLA) and arachidonic acid (AA). These should be included in an amount of about one fourth of the amount of EPA and DHA, for example a ratio of [DHA+EPA] to [DHGLA+AA] of 2.5 to 5.5, preferably 3.3–4.7 wt/wt. The daily dosage of the total of EPA+DHA+DHGLA+AA is preferably at least 120 mg, more preferably at least 350 mg. Per daily dose the preparation in particular contains 20 to 2000 mg, preferably 50 to 1000 mg EPA, 50 to 2000 mg, preferably 200 to 1000 mg DHA and 50 to 2000 mg, preferably 100 to 1000 mg DHGLA.

Further LCPUFA's that can be present are linoleic and α-linoleic acid. However, the ratio of the total amount of EPA+DHA+DHGLA+AA to the total amount of linoleic and α-linoleic acid should be larger than 0.1 wt/wt, preferably larger than 0.2, most preferably larger than 0.4.

As described above fraction b) contains at least two different phospholipids selected from the group consisting of phosphatidylserine, phosphatidylinositol, phosphatidylcholine and phosphatidylethanolamine. Preferably this fraction contains phosphatidylcholine, phosphatidylethanolamine and phosphatidylserine.

The function of this fraction is to provide a direct source of neuronal and endothelial cell phospholipids. It is highly preferred to include a mixture of phospholipids, especially with regard to the choline/ethanolamine moiety couple on the one hand, and the serine/inositol moiety couple on the other hand. For best results the ratio of (phosphatidylcholine and/or phosphatidylethanolamine) to (phosphatidylserine and/or phosphatidylinositol) is 0.5–20 (wt/wt). Per daily dose at least 0.2 g and preferably more than 1 g phospholipids should be administered, for example 4 g.

Another preferred characteristic of the preferred phospholipids is the LCPUFA moiety. It is preferred to use phospholipids which provide the LCPUFA's as described above for fraction a). They can for example be prepared by applying interesterification methods known in the art using for example raw phospholipid mixtures and ingredients that are rich in the particular LCPUFA's. Use of these specific phospholipids ensures a high activity next to a relatively stable product. In preparations for oral use it is not required to use higher organised lipid fractions such as sphingomyelines due to the high metabolic rates of this type of compound in the gut, gut epithelial cells and liver. Also, other lipids, that are essentially free from DHA, EPA, DHGLA or AA, such as neutral triglycerides are preferably not included in the phospholipid fraction or in relatively low amounts, e.g. less than 40% and in particular less than 5% of the lipid fraction. Phospholipids can originate from egg yolk or soy, and can be isolated by applying methods that are known in the art, for example acetone extraction and optionally applying subsequent chromatographic techniques or adsorption methods. The phospholipid fraction can also consist, where required, of mixtures of synthetic phospholipids and (extracts of) phospholipids of natural origin.

Fraction c) contains compounds, which are a factor in methionine metabolism. Total methionine metabolism (TMM) has been described in EP 0 891 719. Though it is known that a proper functioning of TMM is mandatory for the endogenous biosynthesis of many crucial compounds such as S-adenosyl methionine (for creatine, carnitine, etc) and glutathion, and though one has found associations between the occurrence of vascular disorders with hyperhomocysteinaemia, the relevance of a proper functioning of total methionine metabolism for in particular the endothelial cell has not been recognised.

Fraction c) consists of compounds which are a factor in methionine metabolism and contains at least one member selected from the group consisting of folate, vitamin B12, vitamin B6, magnesium and zinc. Preferably this fraction contains at least folate, in particular in an amount equivalent to at least 200 μg and most preferably more than 400 μg folic acid per daily dose. Folate is meant to include physiological equivalents of folic acid such as pharmaceutically acceptable salts thereof, 5-methyltetrahydrofolate and polyglutamate forms thereof as occur naturally. It is most preferred that at least folate and vitamin B6 are included, while the largest part of the population will benefit if these components are simultaneously included. Vitamin B6 should be included in an amount of more than 2 mg, in particular more than 2.5 mg per daily dose. It is even more advantageous when this fraction contains all of the members of the above mentioned group. The fraction can further contain SAMe (S-adenosyl methionine), choline, betaine and/or copper. If fraction c) comprises zinc and copper, the weight ratio of zinc to copper is between 5 to 12. Choline and/or betaine can be included.

In a particularly preferred embodiment of the invention, the preparation additionaly contains hypericin or extract of *Withania somnifera*. Hypericine is also meant to include functional analogues thereof and can be obtained from a plant extract rich in hypericin, such as an extract of *Hypericum perforatum* L. (St. John's wort). The extracts of this plants can suitably be obtained by solvent extraction. Preferably the extraction is carried our with the help of a relatively polar solvent, more preferably the solvent is an alcohol with no more than 5 carbon atoms, e.g. ethanol, methanol or iso-propanol. The extract so obtained is advantageously subjected to a distillation step, preferably under reduced pressure and relatively low temperature, so as to recover most of the extraction solvent.

It was found that the additional inclusion of hypericin in the present preparation enhances its overall efficacy, particularly when said preparation is used to prevent or treat depression. The present invention encompasses the use of the substance hypericin in essentially pure form, as well as natural extracts contain said substance. Preferably the present preparation comprises a natural hypericin containing extract, more preferably such an extract obtained from *Hypericum perforatum*. It was found that significantly better results are obtained with such an extract in comparison to an equivalent amount of pure hypericin, meaning that the extract must contain additional components which synergistically interact with the hypericin present therein.

In addition it was found that best results are obtained if the hypericin containing extract is obtained from fresh plant material, in the case of *Hypericum perforatum* preferably the fresh flowers therefrom, which plant material preferably has not been subjected to a drying step.

In a preferred embodiment of the present method, hypericine or hypericine containing extract is administered in a daily dosage which is equivalent to 0.1–4 mg hypericine, more preferably equivalent to 0.5–2.7 mg hypericin. The extract used in the present method preferably contains from 0.1–2.0% hypericin and is administered in a daily dose of 0.1 to 2 g.

In another embodiment of the invention the method comprises administering a preparation containing hypericin in the form of dried, and optionally milled flowers of *Hypericum perforatum*. Preferably said preparation is administered in a daily dosage that provide a daily amount of between 0.2 and 2 gram of said flowers, calculated on dry weight.

Besides the fractions a) to c) described above, the preparation according to the invention can suitably contain citrate. The term citrate is also meant to include citric acid. The products according to the invention should have a pH between 3.0 and 7.5 and preferably between 5 and 7. Citrate should be administered in an amount of 0.5 to 30 g, preferably 1.5 to 10 g per daily dose, for example more than 2.4 g.

In the biochemistry literature one can find that citric acid, as well as some other compounds, provides reducing equivalents to the cytosol and participates in the "Krebs cycle", thus yielding NADH and energy in the mitochondriae. It is also known for a long time that citric acid helps regulate glycolyses by feedback inhibition of the phosphofructokinase reaction.

However, it is not recognised that for a proper functioning of vascular endothelial cells it is important to have at the same time sufficient amounts of ATP and reducing equivalents in the form of NADPH available in the cytosol of these cells and that citrate can ensure this to occur, and more effectively than a functional analog like a Krebs cycle intermediate like oxaloacetate, malic acid or fumarate.

The preparation preferably further contains one or more members selected from the group consisting of carnitine, vitamin B1, vitamin B5 and coenzyme Q10 or functional analogues thereof. As functional equivalents of carnitine can be mentioned pharmaceutically acceptable salts thereof or alkanoyl and acyl carnitines [acetyl-L-carnitine], which are particularly useful, or mixtures thereof. Carnitine is advantageously included in products that are meant to be used for patients suffering from dementia syndromes. In these products preferably a lipophilic derivative is used as carnitine source. It is most preferred to use acetyl-L-carnitine. This component provides acetyl groups in the brain for biosynthetic purposes. Carnitine should be included in an amount of 0.1 to 3 g, preferably 0.2 to 1 g per daily dose, Vitamin B5 can be included for instance as calcium pantothenate or other stable form. Preferred dosages are 8 to 80 mg, preferably 12 to 40 mg per daily dose product.

In another preferred embodiment the preparation additionally contains a component with anti-oxidant properties. Preferably the antioxidant is selected from the group consisting of vitamin C, vitamin E, lipoic acid, selenium salts and carotenoids. Another component which may advantageously be included in the present preparation is extract of gingko biloba. This extract is obtained from the leaves and is enriched in flavonoids and especially terpenoids, in particular ginkgolides. It appears for example that an extract that comprises at least 4% ginkgolides is effective.

The preparation according to the invention preferably contains tryptophan, functional analogues thereof or proteins containing tryptophan. If the preparation is a food supplement preferably tryptophan or a functional analogue such as alpha-lactalbumin or 5-hydroxytryptophan is used. If the preparation is a complete feeding a protein fraction should be administered with a large ratio of tryptophan to large neutral amino acids, such as the branched amino acids phenylalanin and tyrosin. A preferred daily dose of tryptophan is 0.1 to 2 g.

A further compound which is advantageously included for the treatment of depression is vitamin D, in particular vitamin D3. Preferred daily dose is between 4 and 40 µg.

The preparation preferably contains the above components in an amount above the recommended daily intake. Per daily dose the preparation of the invention preferably comprises:
at least 120 mg long chain polyunsaturated fatty acids;
at least 200 mg phospholipids;
at least 200 µg folate; and
at least 0.1 mg hypericin and/or at least 100 mg *Withania somnifera* extract
at least 0.5 g citrate.

More preferably, the preparation comprises per daily dose:
at least 20 mg, preferably at least 50 mg eicosapentaenoic acid
at least 50 mg, preferably at least 200 mg docosahexaenoic acid
at least 50, mg preferably at least 100 mg arachidonic acid
at least 0.2 mg, preferably at least 0.5 mg hypericin and/or at least 500 mg, preferably at least 1000 mg *Withania somnifera* extract
at least 200 mg, preferably at least 1000 mg phosphatidylserine
at least 200 µg, preferably at least 400 µg folate
at least 100 mg, preferably at least 200 mg magnesium
at least 5 mg, preferably at least 10 mg zinc
at least 2 mg, preferably at least 2.5 mg vitamin B6
at least 2 µg, preferably at least 4 µg vitamin B12
at least 1.0 g, preferably at least 1.5 g citrate.
at least 2 µg, preferably at least 4 µg vitamin D3

The preparations according to the invention can be used in the treatment and/or prevention of vascular, cardio- and cerebrovascular disorders and a selected range of secondary problems. The nature and impact of the latter depends on the time pattern and degree of decrease of the blood flow and the function of the organ/tissue that is involved. Damage to the endothelial cells may also lead to loss of elasticity and even a local lesion of the blood vessel.

In particular the preparation is suitable for the treatment of depression and related disorder, in particular bipolar or unipolar depression, depressions related to menstruation or menopause, schizophrenia, ADHD, anxiety, insomnia, seasonal affective disorder, [. . . ]

EXAMPLES

Example 1

Capsule for use (three times a day) by persons suffering from vascular disorders, in particular those that also suffer from secondary depression. The capsule is prepared using methods known in the art and comprises as active components:

| | |
|---|---|
| DHA | 50 mg |
| EPA | 75 mg |
| phospholipids* | 250 mg |
| folic acid | 200 µg |
| vitamin B12 | 25 mg |
| Hypericine | 2.5 mg |
| vitamin B1 | 100 mg |
| coenzym Q10 | 10 mg |
| vitamin E | 200 mg |
| Ginkgo biloba | 120 mg |

*phosphatidylcholine 130 mg, phosphatidylserine 120 mg (synthetic)

Example 2

Powder for the improvement of vascular conditions and treatment of secondary disorders such as depression, consisting of

| | |
|---|---|
| soylecithin* | 3 g |
| folic acid | 400 µg |
| vitamin B6 | 3 mg |
| vitamin B12 | 4 µg |
| zinc | 15 mg |
| magnesium | 150 mg |
| citric acid/citrate | 2.2 g |
| (pH of product 7.0) | |
| maltodextrines | to make up a total weight of 10 g |

*phosphatidylcholine:phosphatidylethanolamine:phosphatidylinositol = 24:22:15
more than 50 wt. % of the fatty acid residues in the soylecithin consist of Ω6 polyunsaturated fatty acids such as linoleic acid and α-linolenic acid

Example 3

Muesli-bar of about 25 g based on sugar, cereals and pieces of dried fruit that comprises as active components:

| | |
|---|---|
| soylecithin* | 2 g |
| encapsulated fish oil | 0.6 g |
| Single Cell Oil (Mortierella) | 0.3 g |
| Folio acid | 400 µg |
| pyridoxamine | 3 mg |
| cyanocobalamine | 5 µg |
| zinc oxide | 30 mg |
| magnesium oxide | 200 mg |
| citric acid/citrate pH 6.5 mixture | 2 g |
| Hypericum perforatum extract# | 700 mg |
| Ginkgo biloba extract | 200 mg |
| calcium sulphate | 300 mg |
| vitamin D | 10 µg |

*phosphatidylcholine:phosphatidylethanolamine:phosphatidylinositol = 45:26:14)
extract standardised to 0.3 wt. % hypericine content The bar is coated with a layer of chocolate.

The invention claimed is:

1. A method for treating a person having unipolar depression comprising administering orally to said person a preparation comprising:
   a) long chain polyunsaturated fatty acids comprising ω-3 and ω-6 fatty acids, in an amount of at least 350 mg per day;
   b) a mixture of phospholipids comprising phosphatidylcholine and phosphatidylethanolamine and at least one of phosphatidylserine and phosphatidylinositol, wherein said phospholipids are in a ratio of phosphatidylcholine and phosphatidylethanolamine to phosphatidylserine and phosphatidylinositol is between 0.5:1 and 20:1 (wt/wt), and
   c) at least one compound which is a factor in methionine metabolism, selected from the group consisting of folate, vitamin B12, vitamin B6, magnesium and zinc.

2. The method according to claim 1, wherein the preparation further comprises at least one of hypericin and extract of *Withania somnifera*.

3. The method according to claim 1, further comprising administering citrate in an amount of 0.5 to 30 g per day.

4. The method according to claim 1, wherein the preparation further comprises tryptophan, or a protein containing tryptophan.

5. The method according to claim 1, wherein the ω-3 fatty acids are selected from the group consisting of eicosapentaenoic acid and docosahexaenoic acid and the ω-6 fatty acids are selected from the group consisting of arachidonic acid and dihomogammalinolenic acid.

6. The method according to claim 1, wherein c) contains at least folate and vitamin B6.

7. The method according to claim 1, wherein the preparation further comprises at least one member selected from SAMe, choline, betaine and copper.

8. The method according to claim 1, further comprising administering zinc and copper, wherein the weight ratio of zinc to copper is between 5:1 and 12:1.

9. The method according to claim 1, wherein the preparation further comprises at least one member selected from the group consisting of carnitine, vitamin B1, vitamin B5 and coenzyme Q10.

10. The method according to claim 1, wherein the preparation further comprises at least one antioxidant selected from vitamin C, vitamin E, lipoic acid, selenium salt and carotenoids.

11. The method according to claim 1, wherein the preparation further comprises an extract of ginkgo biloba.

12. The method according to claim 1, wherein the preparation further comprises vitamin D.

13. The method according to claim 1, wherein the preparation comprises folate, citrate, at least one of hypericin and extract of *Withania somnifera*, and wherein the method comprises administering the preparation in an amount which provides a daily dose of:
    at least 120 mg of long chain polyunsaturated fatty acids;
    at least 200 mg phospholipids;
    at least 200 µg folate;
    at least one of at least 0.1 mg hypericin and at least 100 mg extract of *Withania somnifera* and
    at least 500 mg citrate.

14. The method of claim 1 further comprising administering phospholipids in an amount of at least 1 g per day.

15. The method according to claim 1, wherein said ω-3 and ω-6 fatty acids are in a ratio of ω-3 fatty acids to ω-6 fatty acids to about 2.5:1 and 5.5:1 (wt/wt).

16. A method for treating a person having unipolar depression comprising administering orally to said person in need thereof an effective amount of a preparation comprising:
   a) long chain polyunsaturated fatty acids comprising ω-3 and ω-6 fatty acids in an amount of at least 350 mg per day, wherein the ω-3 fatty acids comprise eicosapentaenoic acid and docosahexaenoic acid and the ω-6 fatty acids comprise at least one of arachidonic acid and dihomogammalinolenic acid, and wherein said ω-3 and ω-6 fatty acids are in a ratio of eicosapentaenoic acid and docosahexaenoic acid to arachidonic acid and dihomogammalinolenic acid between 2.5:1 and 5.5:1 (wt/wt);
   b) at least two different phospholipids selected from the group consisting of phosphatidylserine, phosphatidylinositol, phosphatidylcholine and phosphatidylethanolamine, and
   c) at least one compound which is a factor in methionine metabolism, selected from the group consisting of folate, vitamin B12, vitamin B6, magnesium and zinc.

17. The method according to claim 16, wherein the preparation comprises eicospentaenoic acid, docosahexaenoic acid, arachidonic acid, magnesium, zinc, vitamin B6 and vitamin B12 and wherein the method comprises administering the preparation in an amount which provides a daily dose of:
- at least 20 mg eicosapentaenoic acid;
- at least 50 mg docosahexaenoic acid;
- at least 50 mg arachidonic acid;
- at least 200 mg phospholipids;
- at least 200 µg folate;
- at least one of at least 0.2 mg hypericin and at least 500 mg *Withania somnifera* extract;
- at least 100 mg magnesium;
- at least 5 mg zinc;
- at least 2 mg vitamin B6;
- at least 2 µg vitamin 312; and at least 1.0 g citrate.

18. The method for treating unipolar depression according to claim 16, wherein said phospholipids are in a ratio of phosphatidylcholine and phosphatidylethanolamine to phosphatidylserine and phosphatidylinositol of 0.5–20:1 (wt/wt).

* * * * *